United States Patent
Yi et al.

(10) Patent No.: US 9,108,180 B2
(45) Date of Patent: Aug. 18, 2015

(54) CATION-EXCHANGED ZEOLITE CATALYST AND PROCESS FOR PRODUCING MONO-IODO BENZENE THROUGH TRANSIODINATION BY USING IT

(75) Inventors: Yong-Jin Yi, Seoul (KR); Jae-Bong Lim, Yongin-si (KR); Il-Hoon Cha, Anyang-si (KR); Han-Seok Kim, Yongin-si (KR); Yong-Ki Park, Daejeon (KR); Won-Choon Choi, Daejeon (KR); Da-Young Min, Daejeon (KR)

(73) Assignee: SK Chemicals Co., Ltd. (KR)

( * ) Notice: Subject to any disclaimer, the term of this patent is extended or adjusted under 35 U.S.C. 154(b) by 271 days.

(21) Appl. No.: 13/142,903

(22) PCT Filed: Dec. 24, 2009

(86) PCT No.: PCT/KR2009/007803
§ 371 (c)(1),
(2), (4) Date: Sep. 14, 2011

(87) PCT Pub. No.: WO2010/077026
PCT Pub. Date: Jul. 8, 2010

(65) Prior Publication Data
US 2012/0172640 A1    Jul. 5, 2012

(30) Foreign Application Priority Data
Dec. 31, 2008   (KR) .................. 10-2008-0137990

(51) Int. Cl.
*C07C 17/00*     (2006.01)
*B01J 29/06*     (2006.01)
(Continued)

(52) U.S. Cl.
CPC ............. *B01J 29/04* (2013.01); *B01J 29/061* (2013.01); *B01J 29/084* (2013.01); *C07C 17/35* (2013.01); *C07C 17/37* (2013.01); *B01J 29/40* (2013.01); *B01J 29/7007* (2013.01)

(58) Field of Classification Search
CPC ....................................................... B01J 29/04
See application file for complete search history.

(56) References Cited

U.S. PATENT DOCUMENTS

| 4,746,758 A | 5/1988 | Rule et al. |
| 4,788,353 A | 11/1988 | Paparatto et al. |

(Continued)

FOREIGN PATENT DOCUMENTS

| CN | 87106739 A | 4/1988 |
| EP | 0181790 A1 | 5/1986 |

(Continued)

OTHER PUBLICATIONS

Pavia et al. Organic Laboratory Techniques: A Microscale Approach 1990, front matter and front cover, 4 pages.*

(Continued)

*Primary Examiner* — Clinton Brooks
(74) *Attorney, Agent, or Firm* — Schwegman Lundberg & Woessner, P.A.

(57) ABSTRACT

The present invention relates to a cation-exchanged zeolite catalyst for an transiodination and a process for producing mono-iodo benzene by using it. Particularly, the cation-exchanged zeolite catalyst has a molar ratio of Si/Al from 5 to 100 and is ion-exchanged with an alkali metal or an alkaline earth metal in range of 2% to 50% of ion exchange capacity. Further, the process for producing mono-iodo benzene of the present invention comprises the step of performing a transiodination by using the cation-exchanged zeolite catalyst to produce mono-iodo benzene from reactants including benzene and one or more multi-iodo benzenes selected from the group consisting of di-iodo benzene and tri-iodo benzene.

6 Claims, 4 Drawing Sheets

(51) Int. Cl.
*B01J 29/04* (2006.01)
*B01J 29/08* (2006.01)
*C07C 17/37* (2006.01)
*C07C 17/35* (2006.01)
*B01J 29/40* (2006.01)
*B01J 29/70* (2006.01)

(56) References Cited

U.S. PATENT DOCUMENTS

| | | |
|---|---|---|
| 4,788,354 A | 11/1988 | Paparatto et al. |
| 4,792,641 A | 12/1988 | Rule et al. |
| 4,806,698 A | 2/1989 | Rule et al. |
| 4,808,759 A | 2/1989 | Paparatto |
| 4,822,929 A | 4/1989 | Paparatto |
| 2010/0094067 A1 | 4/2010 | Kim et al. |
| 2013/0116484 A1 | 5/2013 | Yi et al. |

FOREIGN PATENT DOCUMENTS

| | | |
|---|---|---|
| EP | 0183579 A1 | 6/1986 |
| JP | 57-077631 A | 5/1982 |
| JP | 58-077830 A | 5/1983 |
| JP | 59-219241 A | 12/1984 |
| JP | 61-016527 A | 5/1986 |
| JP | 61-91142 A | 5/1986 |
| JP | 01-502824 A | 9/1989 |
| JP | 01-502825 A | 9/1989 |
| JP | 01-503067 A | 10/1989 |
| KR | 10-2008-0062251 A | 7/2008 |
| SU | 453392 | 12/1974 |
| SU | 453392 A | 1/1975 |
| WO | WO-88/07510 A1 | 10/1988 |
| WO | WO-88/07511 A1 | 10/1988 |
| WO | WO-88/07512 A1 | 10/1988 |
| WO | WO-2008082082 A1 | 7/2008 |

OTHER PUBLICATIONS

KR-10-2006-0137806 machine translation 2008, 12 pages.*
Kim et al. J. Chem. Soc. Faraday Trans., 1992 88(10), 1489-1495.*
Kuduk et al. The Rigaku Journal, vol. 12, No. 2, 1995 pp. 14-34.*
Min et al. "A Study of Catalysts Deactivation on the Forming Reaction of Mono-Iodobenzene by Transiodination Reaction", 2013 or earlier, p. 1.*
Murakami et al. New Developments in Zeolite Science and Technology, 1986, p. 574.*
"International Application Serial No. PCT/KR2009/007803, Written Opinion mailed Jul. 21, 2010", (w/ English Translation), 8 pgs.
Datta, R. L., et al., "Halogenation. XV. Direct Iodination of Hydrocarbons by Means of Iodine and Nitric Acid", *Journal of the American Chemical Society*, 39, (1917), 435-441.
Uemura, S., et al., "Aromatic Bromination and Iodination with Mixtures of Antimony(V) Chloride and Halogens", *Bulletin of Chemical Society of Japan*, 47(1), 1974), 147-150.
"Chinese Application Serial No. 200980155085.8, Office Action mailed Oct. 9, 2012", 6 pgs.
"International Application Serial No. PCT/KR2009/007803, International Preliminary Report on Patentability dated Aug. 9, 2011", (w/ English Translation), 10 pgs.
"Japanese Patent Application No. 2011-544367, Office Action dated Aug. 20, 2013", 2 pgs.
Min. D.-Y., et al., "Study of catalysts deactivation on the forming reaction of mono-Iodobenzene by transiodination reaction", *Spring Symposium 2009 for the Korean Institute of Chemical Engineers*, in Gwangju, Korea, (Apr. 25, 2009), 1 pg.
"International Application Serial No. PCT/KR2009/007803, International Search Report mailed Jul. 21, 2010", (w/ English Translation), 10 pgs.

* cited by examiner

CATION-EXCHANGED ZEOLITE CATALYST AND PROCESS FOR PRODUCING MONO-IODO BENZENE THROUGH TRANSIODINATION BY USING IT

CROSS REFERENCE TO RELATED APPLICATION

This application is a nationalization under 35 U.S.C. 371 of PCT/KR2009/007803 filed Dec. 24, 2009 and published as WO 2010/077026 A2 on Jul. 8, 2010, which application claims priority to and the benefit of Korean Patent Application No. 10-2008-0137990, filed Dec. 31, 2008, which applications and publication are incorporated herein by reference in their entirety.

FIELD OF THE INVENTION

The present invention relates to a cation-exchanged zeolite catalyst for a transiodination, which exhibits high selectivity for mono-iodo benzene and has enhanced lifetime by improvement of a catalytic activity decline. Further, the present invention relates to a process for producing mono-iodo benzene through transiodination by using the cation-exchanged zeolite catalyst.

DESCRIPTION OF THE RELATED ART

An oxy-iodination that synthesizes iodobenzene from benzene and iodine is carried out slowly. Thus, the oxy-iodination is usually conducted in liquid phase by using an oxidizing agent, for example, nitric acid, acetic acid, hydrogen peroxide, or silver sulfide. The oxy-iodination has been described in JP 558-077830A, U.S. Pat. No. 453,392, Journal of the American Chemical Society, vol. 39, page 437, 1917, and so on.

In the oxy-iodination, other oxidizing agents including iodic acid ($HIO_3$), sulfur trioxide ($SO_3$), and hydrogen peroxide ($H_2O_2$) have also been suggested, but none of them have proven to be more efficient than nitric acid.

An iodination by using metal halides as a catalyst instead of the oxidizing agent has been suggested in the Bulletin of Chemical Society of Japan, vol. 47, page 147, 1974. The method of a direct iodination for benzene in gaseous phase by using zeolite 13X catalyst has been suggested in JP S57-077631A.

JP S59-219241A has suggested a technique for producing an iodobenzene compound through the oxy-iodination of benzene by using a strongly acidic zeolite catalyst (Si/Al>>10) under an oxygen atmosphere.

EP0181790 and EP0183579 disclose techniques for synthesizing iodobenzene by oxy-iodination of benzene in the presence of a zeolite catalyst. EP0181790 suggests the use of ZSM-5 or ZSM-11 zeolite catalyst which has been exchanged with divalent or trivalent cations prior to being introduced, since the rapid decrease of the catalytic activity is caused by the utilization of these zeolites in the acid or alkaline form. EP0183579 suggested the use of X-type or Y-type zeolite in non-acidic form to prevent the inactivation of the catalyst. According to the disclosures of these patents, it is effective to ion-exchange the X-or Y-type zeolite with monovalent, divalent or trivalent alkaline or rare earth cations. In the above two European Patents, mono-iodo benzene (MIB) is produced with selectivity of 90% or higher, and di-iodo benzene (DIB) is produced partially as by-products.

As noted above, many patents have disclosed the methods for selectively preparing iodinated aromatic compounds through oxy-iodination. As shown in Schemes 1 to 3, however, various iodinated aromatic compounds are produced from the oxy-iodination and undesired iodinated aromatic compounds are also produced as by-products.

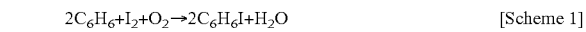   [Scheme 1]

   [Scheme 2]

   [Scheme 3]

Since iodine is very expensive, the production of these iodinated aromatic by-products is economically disadvantageous. Thus, it is required to study the process for converting the iodinated by-products except for MIB and p-DIB into MIB and p-DIB through a transiodination.

The transiodination of the iodinated aromatic compounds have been suggested in U.S. Pat. Nos. 4,792,641, 4,806,698, 4,808,759 and 4,822,929. U.S. Pat. No. 4,792,641 discloses the transiodination of aromatic compounds, particularly DIB, in a gaseous phase at 275~500° C. by using a non-acidic X-type zeolite catalyst that is ion-exchanged with an alkaline metal or alkaline earth metal. U.S. Pat. No. 4,806,698 discloses the transiodination of aromatic compounds, particularly iodonaphthalene, in a liquid phase at 180~250° C. by using an acidic X-, Y-, or L-type zeolite catalyst. However, the methods have a disadvantage of serious inactivation of the catalyst, since iodonaphthalene is only used upon transiodination without a diluting agent such as benzene and naphthalene. U.S. Pat. No. 4,808,759 discloses the transiodination of polyiodobenzene, particularly DIB, at 250~450° C. in the presence of benzene and oxygen by using an X-or Y-type zeolite catalyst that is ion-exchanged with an alkaline or rare earth cations. U.S. Pat. No. 4,822,929 discloses the transiodination of polyiodobenzene, particularly DIB, by using a pentacyl zeolite catalyst that is ion-exchanged with cations of a group II, III or IV metal.

As described in the above listed patents, the zeolite catalysts such as non-acidic X, Y, L or ZSM-5 has been mostly used. In addition, the reaction conditions such as reaction temperature and reactant composition are different depending on the kinds of aromatic compounds, for example, benzene and naphthalene. However, it has not been studied sufficiently for the reaction. In particular, a method of improving the selectivity of the product and the stability of the catalyst needs to be further studied.

Therefore, the present inventors have made extensive studies to develop a catalyst, which exhibits the high selectivity for mono-iodo benzene and the enhanced catalytic activity during the transiodination, and a process for producing mono-iodo benzene by using the catalyst, thereby completing the present invention.

SUMMARY OF THE INVENTION

It is an object of the present invention to provide a cation-exchanged zeolite catalyst for a transiodination, which exhibits high selectivity for mono-iodo benzene and enhanced catalytic activity despite conducting the reaction for a long time.

It is another object of the present invention to provide a process for producing mono-iodo benzene by using the cation-exchanged zeolite catalyst.

DETAILED DESCRIPTION OF THE EMBODIMENTS

The present invention provides cation-exchanged zeolite catalyst for the transiodination of reactants containing multi-iodo benzene and benzene, wherein a molar ratio of Si/Al is 5 to 100 and 2% to 50% of ion exchange capacity is ion-exchanged with an alkali metal or an alkaline earth metal.

Further, the present invention provides a process for producing mono-iodo benzene by using the cation-exchanged zeolite catalyst.

Hereinafter, the cation-exchanged zeolite catalyst and the process for producing mono-iodo benzene by using the catalyst according to the specific embodiment of the present invention will be described in detail.

The cation-exchanged zeolite catalyst according to one embodiment of the present invention is a zeolite catalyst used in the transiodination of reactants containing multi-iodo benzene and benzene, in which a molar ratio of Si/Al is 5 to 100 and 2% to 50% of the ion exchange capacity is ion-exchanged with an alkali metal or an alkaline earth metal.

The term 'multi-iodo benzene', as used herein, means that one or more hydrogens of benzene are substituted with iodine, for example, mono-iodo benzene, di-iodo benzene, and tri-iodo benzene. In addition, the term 'transiodination', as used herein, means a reaction comprising the intramolecular movement (isomerization) or intermolecular movement of iodine atoms contained in the molecule. The transiodination can be usefully applied for the production of mono-iodo benzene (MIB) and para-di-iodo benzene (p-DIB), which are used as a starting material for the synthesis of a high value engineering polymer, for example, poly phenyl sulfide (PPS). Oxy-iodination and transiodination should be combined to effectively produce a main material of PPS, namely, p-DIB from benzene and iodine, which may comprise a reaction process schematically illustrated in FIG. 1.

Figure 1:
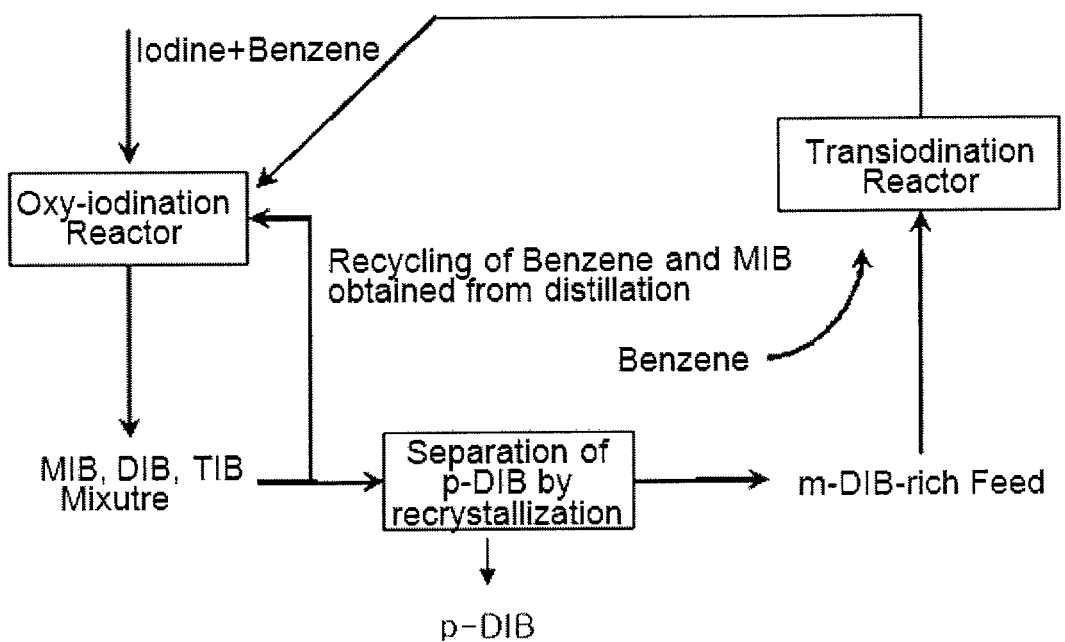
FIG. 1 is a schematic diagram showing the transiodination process according to one embodiment of the present invention.

In accordance with the schematic diagram of FIG. 1, the oxy-iodination of benzene and iodine produces p-DIB. Among the by-products produced through the reaction, benzene and MIB are transferred to an oxy-iodination reactor through a distillation process. Multi-iodo benzenes among the by-products, for example, meta-di-iodo benzene (m-DIB), ortho-di-iodo benzene (o-DIB), and tri-iodo benzene (TIB) are separated from crystallized p-DIB, and transferred to a transiodination reactor to be converted into MIB. As described above, MIB converted through the transiodination reactor is transferred to the oxy-iodination reactor. Even though the by-products such as m-DIB, o-DIB, and TIB are produced, they are efficiently recovered and reused without loss of iodine through such processes according to the present invention.

There is the key aspect of the present invention in the oxy-iodination and the transiodination. In particular, the present invention is characterized by the transiodination of m-DIB, o-DIB, and TIB, which are produced as by-products of the oxy-iodination. Loss of iodinated aromatic compounds in the above reactions causes serious economic problems. Thus, to minimize the loss of iodine, studies on oxy-iodination and transiodination are required, and the cation-exchanged zeolite catalyst according to the above embodiment can be used as a catalyst suitable for the reactions.

The cation-exchanged zeolite catalyst according to the above embodiment of the present invention will be described in more detail below. The cation-exchanged zeolite catalyst can be used for the production of MIB and p-DIB, preferably MIB, through the transiodination reaction. Specifically, during the process for the transiodination, the cation-exchanged zeolite catalyst exhibits high selectivity for mono-iodo benzene, and does not lose its catalytic activity for a long reaction time, thereby enhancing the lifetime of the catalyst.

In this connection, the cation-exchanged catalyst may have a molar ratio of Si/Al within the above range, and preferably a molar ratio of Si/Al of 5 to 15. The catalyst having a molar ratio of Si/Al ranging from 5 to 15 is advantageous to improve the catalytic activity for transiodination.

Further, the alkali metal or alkaline earth metal used in the cation exchange may be, but is not particularly limited to, preferably sodium (Na) or potassium (K). The degree of the cation exchange may be determined within the range from 2% to 50% of the total ion exchange capacity, depending on the cation type of alkali metal or alkaline earth metal to be exchanged. Upon conducting the cation exchange with sodium (Na) ion, the preferred ion exchange capacity is 20% to 50% of the total ion exchange capacity. Upon conducting the cation exchange with potassium (K) ion, the preferred ion exchange capacity is 10% to 50% of the total ion exchange capacity. When the transiodination is carried out by using a catalyst that is cation-exchanged within the above range, a higher selectivity for mono-iodo benzene and a less reduced catalytic activity are observed. If the ion exchange capacity is less than 2%, the effect in the catalytic activity cannot be obtained. If the ion exchange capacity is more than 50%, acidic sites of the catalyst are too reduced, leading to the decline of the transiodination activity.

Specific reaction conditions and procedures for the cation exchange reaction by using the alkali metal or alkaline earth metal are not particularly limited, but the cation exchange reaction may be performed under the conditions well known to be applied in the ion exchange reaction of zeolite catalyst.

Meanwhile, the catalyst for preparing the cation-exchanged zeolite according to the embodiment of the present invention may be selected from the group consisting of Y, BEA, and ZSM-5 zeolites, and then may be cation-exchanged with alkali metal or alkaline earth metal. In particular, the catalyst for preparing the cation-exchanged zeolite is a solid acid catalyst such as zeolite, which is characterized by acidity and pore structure. High acidity of the zeolite catalyst may be generated by ion-exchanging with ammonium ions and the following calcinating to be converted into hydrogen ions. Exemplary zeolite catalysts are Y, BEA, ZSM-5, Mordenite or the like. To control the acidity and pore size, the catalyst may be ion-exchanged with or supported by transition metals, rare earth metals, alkaline metals, alkaline earth metals or the like. In order to produce the catalyst according to the embodiment of the present invention, the cation exchange reaction is preferably carried out by using a $H^+$-type zeolite, which is ion-exchanged with hydrogen ions. For example, the acidic zeolite catalysts such as HY, HBEA, HZSM-5 may be used.

The process for producing mono-iodo benzene according to other embodiment of the present invention comprises the step of performing a transiodination by using a cation-exchanged zeolite catalyst, wherein the multi-iodo benzene is one or more selected from the group consisting of di-iodo benzene and tri-iodo benzene, and the catalyst has a molar ratio of Si/Al from 5 to 100 and is ion-exchanged with an alkali metal or an alkaline earth metal in the range of 2% to 50% of ion exchange capacity.

In this connection, it is preferable that the cation-exchanged zeolite, catalyst has a molar ratio of Si/Al of 5 to 15. In addition, the alkali metal or alkaline earth metal may be, but is not particularly limited to, selected from sodium and potassium. If sodium is selected, the preferred ion exchange capacity may be 20% to 50% of the total ion exchange capacity. If potassium is selected, the preferred ion exchange capacity may be 10% to 50% of the total ion exchange capacity.

As described above, the basic catalyst used in the cation exchange may be preferably any one selected from the group consisting of Y, BEA, and ZSM-5 zeolites.

Meanwhile, the multi-iodo benzene, which is a reactant used in the production of mono-iodo benzene, is preferably a remnant obtained by removing mono-iodo benzene and p-di-iodo benzene from the reaction products resulting from oxy-iodination of benzene, iodine, and oxygen, and more preferably includes one or more selected from the group consisting of m-di-iodo benzene, o-di-iodo benzene, and tri-iodo benzene.

In the production of mono-iodo benzene according to the above embodiment, when benzene is added to the reactant multi-iodo benzene, the selectivity to MIB is improved and inactivation of the catalyst is hindered. In particular, the added benzene plays an important role in the reduction of inactivation speed of the catalyst. As the amount of benzene included in the reactant is increased, the catalyst inactivation is retarded and the selectivity to MIB is improved.

Therefore, in order to increase the selectivity to MIB produced through the transiodination and to reduce the catalyst inactivation, a molar ratio of benzene/multi-iodo benzene is preferably 2:1 or more, and more preferably 3:1 or more for higher selectivity to MIB, and most preferably 25:1 or less for sufficient supply of iodine. The addition of benzene to the reactant plays a key role in stable production of MIB from multi-iodo benzene.

In the transiodination reaction, other reaction conditions except for the catalyst and reactant are not particularly limited, but the reaction temperature is more important than other reaction conditions.

As the reaction temperature becomes low, initial selectivity to MIB is improved due to the decreased side-reaction, but the catalyst activity may be rapidly decreased due to coke deposited in the catalyst. If the reaction temperature is excessively high, the temperature needs to be optimized because of the decreased selectivity to MIB. Thus, the transiodination of the present invention is preferably performed at 120 to 250° C. and more preferably at 160 to 200° C. in order to maintain the selectivity to MIB and the catalyst activity.

In addition to the reaction temperature, the reaction pressure is also a very important factor in terms of catalyst inactivation. It is preferable that the reaction pressure is maintained below a predetermined level. That is, the reaction pressure is very preferably maintained to be lower than the pressure at which benzene contained in the reactant exists not in liquid phase but in gas phase. If the reaction pressure is higher than the pressure, it is possible to accelerate the catalyst inactivation. Thus, the reaction pressure is preferably maintained at atmospheric pressure within the reaction temperature of 120 to 250° C., and is preferably maintained at 10 atm or lower, at which benzene can be liquefied, in order to prevent the catalyst inactivation.

However, if the transiodination of the present invention is performed for a long time, the reaction activity and the selectivity to MIB can be reduced after a specific time period.

It is suggested that the reduced catalyst performance is attributed to coke deposition, and the catalyst activity is rapidly reduced when the amount of coke deposition exceeds a certain range. It is very difficult to prevent the coke deposition in the catalyst. Thus, it is important to minimize the rate of coke deposition for the extension of the catalyst lifetime. It is preferable that the catalyst is reused after a recycling process in order to remove the deposited coke, when the catalyst activity is reduced due to coke deposition.

In this regard, the inactivated catalyst is preferably reused by calcination at 400 to 650° C. under an oxygen or air atmosphere.

In the production of mono-iodo benzene, the cation-exchanged zeolite catalyst of the present invention exhibits high selectivity for mono-iodo benzene and hardly loses its catalytic activity for a long reaction time. Thus, it can be effectively used in the transiodination process and production of mono-iodo benzene.

EXAMPLES

Hereinafter, the functions and the effects of the invention are explained in more detail, according to specific examples of the present invention. However, the following examples are only for explaining the present invention and the range of the present invention is not limited to or by them.

Examples 1~2

Cation/Na Exchanged Zeolite Catalyst $Na^+$-exchanged zeolite catalysts of Examples 1 and 2 were prepared by ion-exchanging by using 0.05 N NaCl. Briefly, the ion-exchange was performed at 60° C. by using 0.05 N NaCl in range of the contents corresponding to 20% (Example 1) and 30% (Example 2) of Albemarle Y411 (Si/Al=5.5) zeolite catalyst, respectively, and followed by washing with distilled water. This procedure was repeated once, and the catalysts were dried in an oven at 110° C. Then, the ion-exchanged catalysts were calcinated under an air atmosphere at 550° C. to prepare $Na^+$-exchanged zeolite catalysts.

Examples 3~4

Cation/K Exchanged Zeolite Catalyst $K^+$-exchanged zeolite catalysts of Examples 3 and 4 were prepared by ion-exchange by using 0.05 N $KNO_3$. Briefly, ion-exchange was performed at 60° C. by using 0.05 N $KNO_3$ in range of the contents corresponding to 10% (Example 3) and 20% (Example 4) of Albemarle Y411 (Si/Al=5.5) zeolite catalyst, respectively, and followed by washing with distilled water. This procedure was repeated once, and the catalysts were dried in an oven at 110° C. Then, the ion-exchanged catalysts were calcinated under an air atmosphere at 550° C. to prepare $K^+$-exchanged zeolite catalysts.

Comparative Example 1

Non-Cation Exchanged Zeolite Catalyst

Albemarle Y411 (Si/Al=5.5) zeolite catalyst was used as a catalyst for Comparative Example 1.

Experimental Example 1

Transiodination by Using Zeolite Catalyst

By using the zeolite catalysts prepared in Examples 1~4 and Comparative Example 1, transiodination was performed under the following conditions.

First, to prevent the loss of a reaction pressure and the channeling of reaction product, the powdery catalyst was pressed by using a press, and then pulverized to granules in the range of 300~800 μm.

1 g of the granulated catalyst was introduced into a reactor, which was made by a stainless steel tubular type and has a diameter of ¾", and then the reaction was carried out.

The catalyst was pretreated by supplying dry air in the flow rate of 100 ml/min at 550° C. for 2 hours. The input rate of reactant was 1 ml/h, while supplying nitrogen as a carrier gas at a flow rate of 6 ml/min.

The transiodination was performed with the reactants including Benzene and one or more multi-iodo benzenes. The multi-iodo benzenes were comprised of m-DIB and o-DIB as a major ingredient and MIB, p-DIB, and TIB as a minor ingredient. In the reactants, the multi-iodo benzene and benzene were mixed in the weight ratio of 3:7 (the molar ratio of benzene/multi-iodo benzene was 16.5:1). The multi-iodo benzenes contained in the reactants (hereinbelow, referred to as "feed"), used for this experiment, was a remnant obtained by separating MIB and p-DIB from the products by oxyiodination of benzene and iodine. The components in the feed were analyzed by gas chromatography (GC) equipped with an AT-35 column and an FID detector.

Under the above reaction conditions, based on 1 g of the catalysts prepared in Examples 1~4 and Comparative Example 1, the reactant was introduced in the feed rate of 1 ml/hr and reacted at 250° C. and 1 atm. The reaction products were collected according to the passage of time, and a molar ratio (mol %) of each component was analyzed and the result are shown in the following Table 1.

TABLE 1

| Section | Catalyst | Time (h) | MIB | p-DIB | m-DIB | o-DIB | TIB |
|---|---|---|---|---|---|---|---|
| Example 1 | 20% Na/HY(5.5)* | 32 | 96.5 | 0.9 | 2.1 | 0.5 | 0 |
| | | 44 | 93.1 | 1.3 | 4.8 | 0.6 | 0.2 |
| | | 57 | 86.9 | 1.1 | 10.6 | 0.9 | 0.5 |
| | | 65 | 75.5 | 1.6 | 18.4 | 2.8 | 1.7 |
| Example 2 | 30% Na/HY(5.5)* | 33 | 96.9 | 0.8 | 2 | 0.3 | 0 |
| | | 49 | 93.8 | 1 | 4.2 | 0.6 | 0.4 |
| | | 66 | 82.1 | 1.3 | 14.2 | 1.8 | 0.6 |
| | | 72 | 65.6 | 2.1 | 24.7 | 4.4 | 3.2 |
| Example 3 | 10% K/HY(5.5)* | 30 | 94.3 | 1.2 | 3.8 | 0.6 | 0.1 |
| | | 41 | 91.9 | 1.3 | 5.9 | 0.7 | 0.2 |
| | | 51 | 86.3 | 1.5 | 10.6 | 1 | 0.6 |
| | | 74 | 66.4 | 1.6 | 26.3 | 3 | 2.7 |
| Example 4 | 20% K/HY(5.5)* | 31 | 94 | 1.6 | 3.5 | 0.8 | 0.1 |
| | | 48 | 91 | 1.3 | 6.8 | 0.6 | 0.3 |
| | | 55 | 88.4 | 1.3 | 9.3 | 0.7 | 0.3 |
| | | 67 | 74.5 | 0.9 | 21.4 | 1.9 | 1.3 |
| Comparative Example 1 | HY(5.5)* | 30 | 95.2 | 1.1 | 3.2 | 0.5 | 0 |
| | | 39 | 92.5 | 1.2 | 5.6 | 0.7 | 0 |
| | | 54 | 84.7 | 1.2 | 11.3 | 1.7 | 1.1 |
| | | 70 | 58.9 | 2.6 | 28.2 | 5.6 | 4.7 |

*(numerical value) represents a molar ratio of Si/Al.

Figure 2:
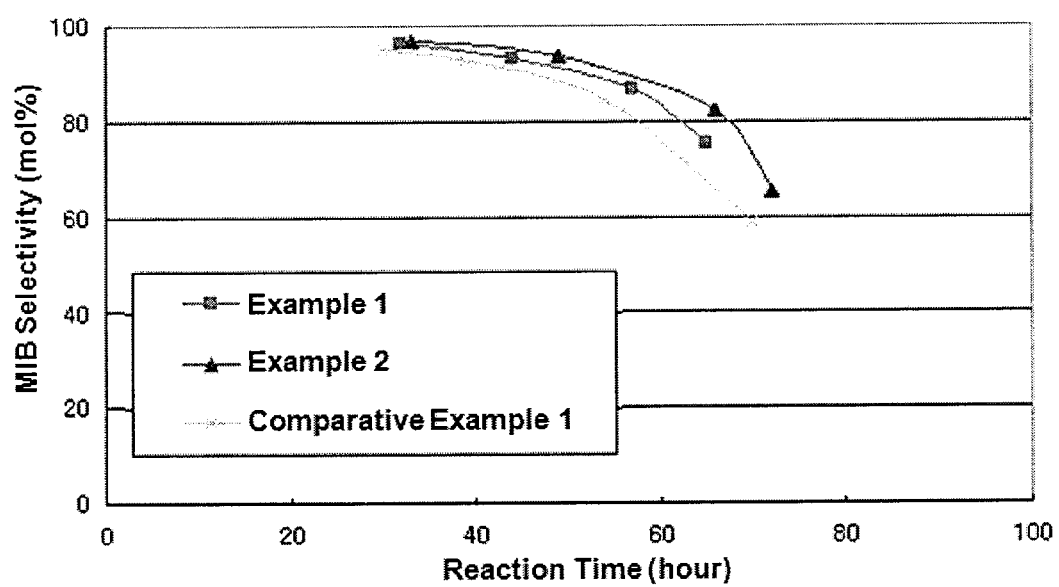
FIG. 2 is a graph showing mono-iodo benzene selectivity according to time in the production of mono-iodo benzene by using the zeolite catalyst that is ion-exchanged with sodium (Na) according to one embodiment of the present invention.

MIB selectivities of the Na$^+$-exchanged zeolite catalysts of Examples 1 and 2 and non-cation exchanged zeolite catalyst of Comparative Example 1 according to reaction time were compared and shown in FIG. 2. As shown in FIG. 2, the Na$^+$-exchanged zeolite catalysts of Examples 1 and 2 showed excellent values in the reaction activity and MIB selectivity, compared to the non-cation exchanged zeolite catalyst of Comparative Example 1. In particular, among the catalysts of Examples 1 and 2, the catalyst of Example 2 with higher extent of ion-exchange showed higher MIB selectivity and less reduction in catalytic activity according to reaction time.

Figure 3:
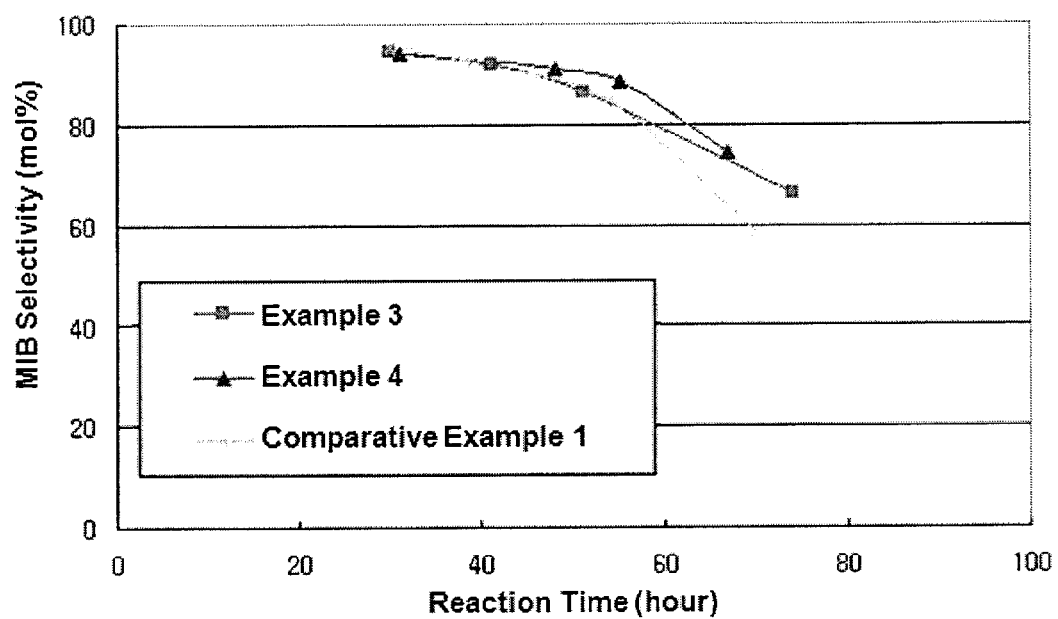
FIG. 3 is a graph showing mono-iodo benzene selectivity according to time in the production of mono-iodo benzene by using the zeolite catalyst that is ion-exchanged with potassium (K) according to one embodiment of the present invention.

Meanwhile, MIB selectivities of the K$^+$-exchanged zeolite catalysts of Examples 3 and 4 and non-cation exchanged zeolite catalyst of Comparative Example 1 according to reaction time were compared and shown in FIG. 3. As shown in FIG. 3, the catalyst of Example 3 having K$^+$-ion exchange ratio of 10% showed initial MIB selectivity similar to that of Albemarle Y411 (Si/Al=5.5) zeolite catalyst of Comparative Example 1, but showed less reduction in its activity for a long period of reaction time. Further, the catalyst of Example 4 having K$^+$-ion exchange ratio of 20% showed excellent values in the reaction activity and MIB selectivity, compared to Albemarle Y411 (Si/Al=5.5) zeolite catalyst of Comparative Example 1.

As shown in Table 1, in particular, the catalysts of Examples 1 to 4 showed a high MIB selectivity of 66.4% to 75.5 mol % for a long reaction time of 65 hrs or longer, while the catalyst of Comparative Example 1 showed a lower MIB selectivity of 58.9 mol % for a long reaction time of 65 hrs or longer. That is, the catalytic activity of Comparative Example 1 is greatly reduced, as reaction time is longer.

Experimental Example 2

Transiodination by Regenerating an Inactivated Catalyst

In the transiodination by using the zeolite catalyst of Example 1, the reaction was performed by using the regerated catalyst, which was prepared by calcinating an inactivated catalyst at 500° C. under air atmosphere, to produce mono-iodo benzene. The transiodination and analysis were carried out in the same manner as in Experimental Example 1, except for using the regenerated catalyst that was prepared by calcinating the inactivated catalyst.

Figure 4:
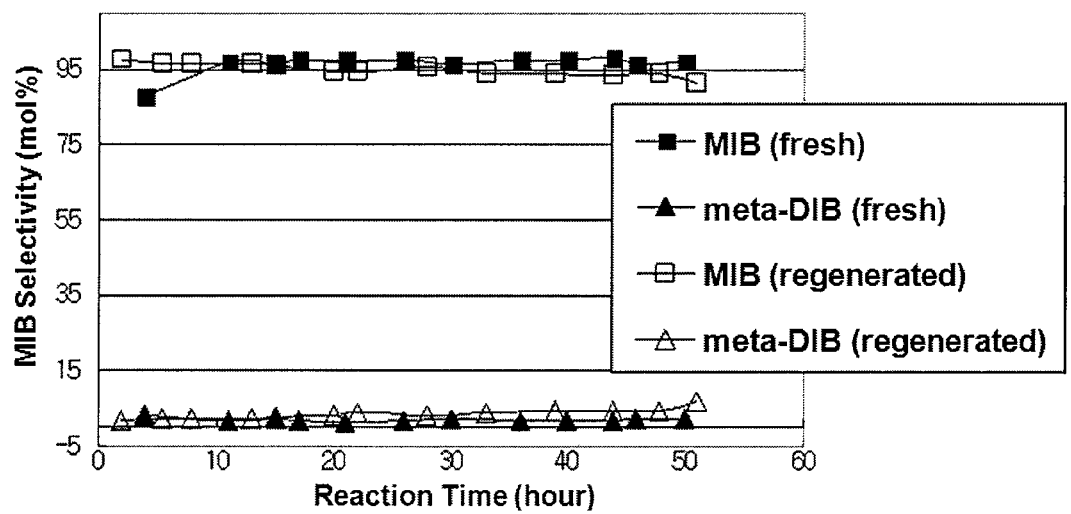
FIG. 4 is a graph showing mono-iodo benzene selectivity according to time in the production of mono-iodo benzene by using the zeolite catalyst that is ion-exchanged with sodium (Na) according to one embodiment of the present invention, wherein the catalyst is regenerated by calcinating an inactivated catalyst.

A molar ratio [mol %, MIB/meta-DIB(Regenerated)] for each component of reaction products produced by using the regenerated catalyst prepared from the inactivated catalyst is shown in FIG. 4. Also, a molar ratio [mol %, MIB/meta-DIB (Fresh)] of each component of reaction products produced by using the fresh zeolite catalyst of Example 1 before inactivation is shown together with that for the regenerated catalyst.

As shown in FIG. 4, even though the Na$^+$-exchanged zeolite catalyst of Example 1 was regenerated by calcinating, it also showed the consistent activity and excellent values in the MIB selectivity. Therefore, it can be seen that recycling of the inactivated cation-exchanged zeolite catalyst of the present invention does not adversely affect the selectivity for mono-iodo benzene and catalytic activity.

As compared with the experimental results between Examples 1~4 and Comparative Example 1, the cation-exchanged zeolite of the present invention exhibits high selectivity for mono-iodo benzene and hardly loses its catalytic activity for a long reaction time during transiodination reaction, thereby being useful in the production of mono-iodo benzene through transiodination.

What claimed is:
1. A catalyst comprising:
   a cation-exchanged Y zeolite having a molar ratio of Si/Al is 5 to 100 wherein:

20% to 50% of the cation exchange capacity of the cation-exchanged Y zeolite is exchanged with sodium cation ($Na^+$); or 10% to 50% of the cation exchange capacity of the cation-exchanged Y zeolite is exchanged with potassium cation ($K^+$).

2. The catalyst according to claim 1, wherein the molar ratio of Si/Al is 5 to 15.

3. The catalyst according to claim 1, wherein 20% to 30% of the cation exchange capacity is cation-exchanged with sodium cation ($Na^+$).

4. The catalyst according to claim 1, wherein 10% to 20% of the cation exchange capacity is cation-exchanged with potassium cation($K^+$).

5. The according to claim 1, which is used for producing mono-iodo benzene through a transiodination.

6. The catalyst according to claim 1, wherein the cation-exchanged Y zeolite is Y411.

* * * * *